United States Patent
Singer et al.

(10) Patent No.: US 10,828,242 B2
(45) Date of Patent: Nov. 10, 2020

(54) ARTIFICIAL SWEAT COMPOSITION

(71) Applicants: Symrise AG, Holzminden (DE); Monell Chemical Senses Center, Philadelphia, PA (US)

(72) Inventors: Marco Singer, Holzminden (DE); Keith McDermott, Bound Brook, NJ (US); Marcela Olalde-Castillo, Park Ridge, NJ (US); George Preti, Horsham, PA (US); Charles Wysocki, Collingswood, NJ (US); Katherine Ashley Prigge, Philadelphia, PA (US)

(73) Assignees: Symrise AG, Holzminden (DE); Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 15/763,344

(22) PCT Filed: Oct. 22, 2015

(86) PCT No.: PCT/EP2015/074551
§ 371 (c)(1),
(2) Date: Mar. 26, 2018

(87) PCT Pub. No.: WO2017/054892
PCT Pub. Date: Apr. 6, 2017

(65) Prior Publication Data
US 2019/0105250 A1    Apr. 11, 2019

Related U.S. Application Data

(60) Provisional application No. 62/234,898, filed on Sep. 30, 2015.

(51) Int. Cl.
*A61K 8/36*     (2006.01)
*A61K 8/46*     (2006.01)
*A61Q 15/00*    (2006.01)
*A61K 8/02*     (2006.01)
*A61K 8/33*     (2006.01)
*A61K 8/365*    (2006.01)
*G01N 33/483*   (2006.01)

(52) U.S. Cl.
CPC ............... *A61K 8/361* (2013.01); *A61K 8/02* (2013.01); *A61K 8/33* (2013.01); *A61K 8/36* (2013.01); *A61K 8/365* (2013.01); *A61K 8/46* (2013.01); *A61Q 15/00* (2013.01); *A61K 2800/872* (2013.01); *G01N 33/483* (2013.01)

(58) Field of Classification Search
CPC .... A61Q 15/00; A61K 2800/872; A61K 8/02; A61K 8/33; A61K 8/36; A61K 8/361; A61K 8/365; A61K 8/46
See application file for complete search history.

(56) References Cited

FOREIGN PATENT DOCUMENTS

| EP | 1553411 A1 | 7/2005 | |
|---|---|---|---|
| JP | 20044263102 A | 9/2004 | |
| JP | 2005062159 A | 3/2005 | |
| JP | 2005105250 A | 4/2005 | |
| WO | WO-2004078154 A1 * | 9/2004 | ............. A61K 8/922 |

OTHER PUBLICATIONS

English translation of Hirano et al. JP2004263102A 2004; 7 pages. (Year: 2004).*

* cited by examiner

*Primary Examiner* — Ernst V Arnold
(74) *Attorney, Agent, or Firm* — Dilworth & Barrese, LLP

(57) ABSTRACT

The present invention belongs to the area of body odour modelling. In particular, the developed synthetic compositions of the present invention reconstitute human body odours, especially those arising from axillary perspiration. The use of the compositions herein allows for the evaluation of malodour masking effects of fragrant compositions in the field of personal care or homecare products and cosmetic product development.

11 Claims, No Drawings

ARTIFICIAL SWEAT COMPOSITION

FIELD OF THE INVENTION

The present invention belongs to the area of body odour modelling. In particular, the developed synthetic compositions of the present invention reconstitute human body odours, especially those arising from axillary perspiration. The use of the compositions herein allows for the evaluation of malodour masking effects of fragrant compositions in the field of personal care or homecare products and cosmetic product development.

STATE OF THE ART

Fragranced products such as perfumes, deodorants or other fragrance containing personal care or cosmetic products have widely been used to mask unpleasant body odours, in particular the malodour of human sweat. Developing particularly efficient fragrance compositions that are able to overcome bad odours from axillary perspiration is a major challenge. Until now this development heavily relies on expensive and time consuming in vivo studies requiring human test subjects and therefore does not allow for systematic and extensive screening of individual fragrance raw materials or perfume oils. Furthermore working with authentic sweat samples ex vivo is difficult since the odour quality and intensity of those samples changes, making reproducible and consistent measurement over an extended time period difficult. As a result artificially created malodours are of high interest to the field of malodour counteraction. Current approaches involve only single materials known to be present in human axillary secretions like 3-mercapto-3-methyl-hexan-1-ol or simple mixtures of 3-methyl-2-hexenoic acids and 3-hydroxy-3-methyl-hexanoic acid as malodour standards solely relying on analytic investigations of human sweat samples.

WO 2004/078154 A1 discloses pseudo body odour compositions which are close to peculiar odour that an actual body has. The pseudo body odour composition therein, comprises (A) at least one kind selected from (A-1) hydroxyalkanyl carboxylic acids having 5 to 8 carbon atoms and (A-2) alkenyl carboxylic acids having 5 to 8 carbon atoms and one double bond; (B) at least one kind selected from fatty acids having 2 to 24 carbon atoms; and (C) at least one kind selected from aldehydes having 2 to 13 carbon atoms. Component (A-2) is selected from racemic 3-methyl-2-hexenoic acid.

WO 2006/003053 A1 refers to the use of 3-mercapto-3-methyl-hexan-1-ol as malodour standard. The use of the said standard shall allow determination of particularly effective perspiration odour-masking fragrant compositions.

There is therefore a demand for a malodour standard that is based on analytical data as well as sensory evaluation of human sweat extracts in order to closely match genuine human sweat in terms of chemical components and odour quality. In particular, the malodour standard should be chemically stable over an extended period of time in order to produce reproducible results. Furthermore, an object of the invention was to develop specific body odour models compositions which show certain characteristics of sweat odour for different ethnic groups. Especially, an object of the present invention was the development of body odour model compositions that can be used for body odour masking tests that take into account the ethnicity of the targeted consumer groups, thereby allowing a more focused and personalized product development.

DESCRIPTION OF THE INVENTION

A first object of the present invention are artificial sweat odour compositions, comprising a solvent and
(i) at least an alkenoic acid compound having 2-10 carbon atoms,
(ii) at least a saturated aliphatic carboxylic acid compound having 2-15 carbon atoms, and optionally
(iii) at least one saturated aliphatic hydroxyl carboxylic acid compound having 3-10 carbon atoms, and/or
(iv) at least one mercapto-alkanol compound having 2-10 carbon atoms, Surprisingly, analytical and sensory studies with human sweat samples from subjects differing in ethnicity showed distinct chemical compositions and odour profiles depending on the donor's ethnical background. It has been observed that artificial sweat odour compositions have to take into account these differences in order to reliably match and distinguish axillary odours of people from varying origin. Furthermore it has been shown that these new artificial compositions are easily reproducible and stable over time.

In a preferred embodiment of the present artificial sweat odour composition, the compounds (i) to (iv) can be selected from
(i) 7-octenoic acid, 3-methyl-2-hexenoic acid;
(ii) isovaleric acid, 2-methyl butyric acid, hexanoic acid, octanoic acid, nonanoic acid, 4-ethyl octanoic acid, decanoic acid, undecanoic acid, butyric acid, propionic acid, acetic acid;
(iii) 3-hydroxy-3-methylhexanoic acid, lactic acid;
(iv) 3-mercapto-3-methyl-1-hexanol, 3-mercapto-1-hexanol.

In a first preferred embodiment of the present artificial sweat odour composition, the composition comprises
(i) at least 3-methyl-2-hexenoic acid as alkenoic acid compound, and
(ii) at least a mixture consisting of isovaleric acid, hexanoic acid, octanoic acid, nonanoic acid, 4-ethyl octanoic acid, decanoic acid, butyric acid as saturated aliphatic carboxylic acid compounds The thus obtained artificial sweat odour compositions have the advantage to be close to genuine human sweat and most importantly reflect well the odour quality of the typical perspiration odour. Thus, the compositions of the present invention are therefore important in sensory terms for testing malodour counteraction which hitherto relied only on analytic results and did not take into account e.g. ethnic differences in sweat composition.

In a further embodiment of the present invention the said artificial sweat odour composition further comprises at least propionic acid, acetic acid as saturated aliphatic carboxylic acid compound (ii) and at least lactic acid as saturated aliphatic hydroxyl carboxylic acid compound (iii).

Thus, a more specific preferred embodiment of the invention of the artificial sweat odour composition comprises compounds (i) and (ii) and (iii), wherein
(i) the at least alkenoic acid compound is 3-methyl-2-hexenoic acid, and
(ii) the at least saturated aliphatic carboxylic acid compound is a mixture consisting of isovaleric acid, hexanoic acid, octanoic acid, nonanoic acid, 4-ethyl octanoic acid, decanoic acid, butyric acid, propionic acid, acetic acid, and (iii) the at least saturated aliphatic hydroxyl carboxylic acid compound is lactic acid.

The obtained artificial sweat odour composition has the advantage to be representative in terms of sensory properties to the axillary perspiration from people of east East Asian descent.

In a specific composition, particularly directed to people of East Asian descent the artificial sweat odour composition of the present invention comprises
(i) from 0.0001 to 0.6% by weight, preferably 0.001 to 0.3% by weight, more preferably 0.005 to 0.1% by weight alkenoic acid compound which is 3-methyl-2-hexenoic acid, and
(ii) from 0.0001 to 0.20000% by weight saturated aliphatic carboxylic acid compound which is a mixture of 4-ethyl octanoic acid, butyric acid, hexanoic acid, isovaleric acid, nonanoic acid and octanoic acid, acetic acid and propionic acid, and
(iii) from 0.1 to 2.0% by weight saturated aliphatic hydroxyl carboxylic acid compound is lactic acid,
each based on the total weight of the total composition, wherein the total weight of all compounds in the artificial sweat odour composition is less than 3% by weight, preferably less than 2% by weight.

Another preferred embodiment of the above artificial sweat odour composition is further, wherein
(i) the at least alkenoic acid compound further comprises oct-7-enoic, and
(ii) the at least saturated aliphatic carboxylic acid compound further comprises 2-methylbutyric acid, undecanoic acid, butyric acid, and
(iii) the at least saturated aliphatic hydroxyl carboxylic acid compound is 3-hydroxy-3-methylhexanoic acid, and
(iv) the at least one mercapto-alkanol compound is a mixture of 3-mercapto-1-hexanol and 3-mercapto-3-methyl-1-hexanol.

Thus another specific preferred embodiment of the invention of the artificial sweat odour composition comprises compounds (i) and (ii), (iii) and (iv), wherein
(i) the at least alkenoic acid compound is a mixture comprising 3-methyl-2-hexenoic acid and 7-octenoic acid, and
(ii) the at least saturated aliphatic carboxylic acid compound is a mixture of isovaleric acid, 2-methyl butyric acid, hexanoic acid, octanoic acid, nonanoic acid, 4-ethyl octanoic acid, decanoic acid, undecanoic acid, butyric acid, and
(iii) the at least saturated aliphatic hydroxyl carboxylic acid compound is 3-hydroxy-3-methylhexanoic acid, and
(iv) the at least one mercapto-alkanol compound is a mixture of 3-mercapto-1-hexanol and 3-mercapto-3-methyl-1-hexanol.

The thus obtained artificial sweat odour composition has the advantage that it is characteristic of unpleasant sweat odour and body odour of the ethnic group of people of African and/or Caucasian descent.

In a specific composition, particularly directed to people of African descent the artificial sweat odour composition comprises
(i) from 0.001 to 0.6% by weight, preferably 0.01 to 0.3% by weight, and more preferably 0.1 to 0.2% by weight alkenoic acid compound which is a mixture of 3-methyl-2-hexenoic acid and 7-octenoic acid, and
(ii) from 0.01 to 1.0% by weight, preferably 0.1 to 0.5% by weight, more preferably 0.2 to 0.3% by weight saturated aliphatic carboxylic acid compound which is a mixture of isovaleric acid, 2-methyl butyric acid, hexanoic acid, octanoic acid, nonanoic acid, 4-ethyl octanoic acid, decanoic acid, undecanoic acid, butyric acid, and
(iii) from 0.005 to 1.0% by weight, preferably 0.01 to 0.5% by weight, more preferably 0.04 to 0.1% by weight saturated aliphatic hydroxyl carboxylic acid compound which is 3-hydroxy-3-methylhexanoic acid, and
(iv) from 0.000001 to 0.2% by weight, preferably 0.00001 to 0.01% by weight, more preferably 0.00001 to 0.0001% by weight mercapto-alkanol compound which is a mixture of 3-mercapto-1-hexanol, 3-mercapto-3-methyl-1-hexanol,
each based on the total weight of the total composition, wherein the total weight of all compounds in the artificial sweat odour composition is less than 3% by weight, preferably less than 2% by weight.

In another specific composition, particularly directed to people of Caucasian descent the artificial sweat odour composition comprises
(i) from 0.01 to 1.0% by weight, preferably 0.08 to 0.9% by weight, more preferably 0.1 to 0.7% by weight alkenoic acid compound which is a mixture of 3-methyl-2-hexenoic acid and 7-octenoic acid, and
(ii) from 0.01 to 1.2% by weight, preferably 0.1 to 0.8% by weight, more preferably 0.2 to 0.5% by weight saturated aliphatic carboxylic acid compound which is a mixture of isovaleric acid, 2-methyl butyric acid, hexanoic acid, octanoic acid, nonanoic acid, 4-ethyl octanoic acid, decanoic acid, undecanoic acid, butyric acid, and
(iii) from 0.0001 to 1.0% by weight, preferably 0.001 to 0.1% by weight, more preferably 0.003 to 0.01% by weight saturated aliphatic hydroxyl carboxylic acid compound which is 3-hydroxy-3-methylhexanoic acid, and
(iv) from 0.0000001 to 0.2% by weight, preferably 0.000001 to 0.001% by weight, more preferably 0.000008 to 0.0001% by weight mercapto-alkanol compound which is a mixture of 3-mercapto-1-hexanol, 3-mercapto-3-methyl-1-hexanol,
each based on the total weight of the total composition, wherein the total weight of all compounds in the artificial sweat odour composition is less than 3% by weight, preferably less than 2% by weight.

In another preferred embodiment, the artificial sweat odour composition of the present invention comprises a solvent and only compounds (i) and (ii), which are preferably at least
(a) 3-methyl-2-hexenoic acid as alkenoic acid compound having 2-10 carbon atoms; and
(b) a mixture of octanoic acid and nonanoic acid as saturated aliphatic carboxylic acid compound having 2-15 carbon atoms.

This basic composition of at least the three compounds (i) and (ii) is advantageous because it is characteristic of unpleasant sweat odour and body odour of the ethnic group of people of East Asian descent.

In another preferred embodiment, the artificial sweat odour composition of the present invention comprises a solvent and only compounds (i), (iii) and (iv), which are preferably at least
(a) 3-methyl-2-hexenoic acid as alkenoic acid compound having 2-10 carbon atoms; and
(b) 3-hydroxy-3-methylhexanoic acid as saturated aliphatic hydroxyl carboxylic acid compound having 3-10 carbon atoms, and
(c) 3-mercapto-3-methyl-1-hexanol as mercapto-alkanol compound having 2-10 carbon atoms.

This basic composition of at least the three compounds (i), (iii) and (iv) is advantageous because it is characteristic of unpleasant sweat odour and body odour of the ethnic group of people of African and/or Caucasian descent.

The advantage of the present artificial sweat odour model composition is the reproducibility and the simple interchangeability from one ethnic group to another by adjusting the amount of certain compounds and/or changing of certain compounds as described herein before mentioned.

Preferred solvents used in the artificial sweat odour composition of the present invention are selected from trialkyl citrates such as triethylcitrat (TEC), trimethyl citrate, tripropyl citrate, tri-isopropyl citrate, tributyl citrate, tri-isobutyl citrate, tri-sec.-butyl citrate, dialkylphthalates such as dimethylphtahalat, diethylphtalat (DEP), dibutylphthalat, benzylbenzoat, isopropylmyristate, dioctyladipat, alcohols such as 1,2-alkandiols such as 1,2-butadiol, 1,2-pentandiol, 1,2-hexandiol, 1,2-heptanddiol, 1,2-octandiol, 1,2-nonandiol, 1,2-decandiol, 1,2-undecandiol, 1,2,dodecandiol, ethanol, fatty oils, such as cooking oils and in particular vegetable oils such as for example borage oil, thistle oil, groundnut oil, hazelnut oil, coconut oil, pumpkin seed oil, linseed oil, maize germ oil, macadamia nut oil, almond oil, olive oil, pecan nut oil, pistachio kernel oil, rapeseed oil, rice germ oil, sesame seed oil, Soya oil, sunflower oil, walnut oil or wheat germ oil, fractionated coconut oils, which mainly have fatty acid residues with a length of between six and eight carbon atoms (C6- to C8-fatty acids), propylene glycol, diacetine (glycerine diacetate), triacetine (glycerine triacetat), benzyl alcohol, triethyl citrate, ethyl lactate, isopropanol and glycerine, mineral oil.

The preferred 1,2-alkandiol is 1,2-pentandiol, 1,2 aliphatic alcohols such as ethanol, n-propanol, isopropylalcohol, the isomeric butanols and mixtures thereof.

The used solvents preferably dissolve compounds (i) to (iv), thus a homogenous composition could be obtained.

Preferably, the total amount of all compounds (i) to (iv) in the artificial sweat odour model composition is in the range from 0.1-5% by weight, preferably 0.3 to 2.1% by weight, preferably 0.4 to 1.9% by weight, more preferably 0.45 to 1.5% by weight, based on the total weight of the composition, and thus the solvent sums up the total weight of the composition to 100% by weight.

The compounds (i) to (iv) are in fact only present in very small quantities in human sweat but produces an extremely strong odour impression and exhibit in some cases a very low threshold value. In addition, it is characteristic of the bad odour impression of body sweat. It is therefore particularly suitable for use as a malodour standard. In higher concentrations, a very sweaty and also sulphurous, musty note is perceivable.

A further object of the present invention is the use of the artificial sweat odour compositions of the present invention as already described herein as a malodour standard.

Another further object of the present invention is the use of an artificial sweat odour composition as already described herein for evaluating an effect of masking, harmonizing or deodorizing the odor of sweat.

Further object of the present invention is the use of an artificial sweat odour composition as already described herein for evaluating the cleaning efficiency of cleaning agents, such as for skin, hair and laundry.

Another object of the present invention is the use of an artificial sweat odour composition as already described herein for the production of a malodor standard.

A further object of the invention is a scent/smell stick or spray comprising the artificial sweat odour composition as already described herein, in particular for use to evaluate an effect of masking, harmonizing or deodorizing the odour of sweat, especially human sweat. In particular, an object is the use of such a scent/smell pen or spray as malodour standard to train a sensory panel group.

Using a scent/smell stick, pen or spray in which the artificial sweat odour composition is filled have the advantage that the malodour model is portable and is easy to provide to customers. The scent/smell stick or pen in which the artificial sweat odour composition is filled is constructed just likely to a felt pen or marker, in which the imitated sweat odour composition is filled in the pen or stick instead of colour solution. Such a pen or stick is a benefit to train or practice for a sensory panel group (a group of test persons for a sensory test), in this case especially to train on sweat intensity and sweat odour, in particular in terms of specific ethnic sweat odour groups.

Actually the artificial sweat odour composition can be administered in any form such as a spray, gel, foam, ointment, tincture, lotion, cream, milk, oil or stick. In any case the important aspect is that the artificial sweat odour composition can be used as a malodour standard.

A further object of the invention is therefore a test procedure for evaluating an effect of masking, harmonizing or deodorizing to a body odor by a sample comprising one or more flavors or fragrances, comprising the steps:
(a) providing an artificial sweat odour composition as described herein before mentioned,
(b) bringing the artificial sweat odor composition of step a) in contact with a flavor or fragrance sample which should be evaluated,
(c) determining the intensity and/or malodour impression of the artificial sweat odor composition in comparison to the flavor or fragrance sample which is to be evaluated.

The said procedure is not restricted to a certain kind of testing applicator. A possibility way is to formulate the artificial sweat odour composition into a stick, which can be smelt by flavours experts or test persons. Another way is to use a spray, in which the artificial sweat odour composition is included to muster the malodour standard e.g. onto a surface such as a hard surface, paper, textile, outerwear or clothes. Any way to use the artificial sweat odour composition of the present invention as model composition should be possible and should not underlying any restrictions by not explicitly being described herein.

A further object of the invention is a method of evaluating a masking, harmonizing or deodorizing effect to a sweat odour, characterized by using the artificial sweat odour composition of the present invention as already described herein.

An advantage of the present invention is that the developed artificial sweat odour compositions can easily be used for testing and evaluating the masking, harmonizing or deodorizing ability of a fragrance/flavour or a fragrance/flavour mixture of perfume, especially in terms of masking, harmonizing or deodorizing of sweat odour or body odour.

Additionally the developed artificial sweat odour compositions of the present invention are usable for evaluating an effect of masking, harmonizing or deodorizing of a fragrance/flavour or a fragrance/flavour mixture or a perfume for skin, hair and laundry products.

In any case, to evaluate the effect of masking, harmonizing or deodorizing of a fragrance/flavour or a fragrance/flavour mixture or a perfume the following method can be applied, but it is not restricted to: In a first step, the developed artificial sweat odour composition of the present invention is applied onto a surface such as a hard surface, paper, textile, outerwear or clothes. Afterwards (second step) the intensity of the artificial sweat odour composition is determined through smelling by trained assessors, thus the malodour or bad odour is detected and evaluated. In a third step, the fragrance/flavour or fragrance/flavour mixture or perfume is applied onto the said surface, e.g. through spraying, and afterwards the intensity of the sweat odour (artificial sweat odour composition) is determined again and can be compared to the odour detection in the second step. Thus, the effectiveness of the reduction of sweat odour can be determined through this method and the use of the developed artificial sweat odour compositions.

To determine the masking, harmonizing or deodorizing effect of a fragrance/flavour or a fragrance/flavour mixture or a perfume on laundry, a fourth step can be included, wherein the outerwear or clothes are washed and then a final determination of sweat odour (artificial sweat odour composition) intensity is accomplished.

Within the framework of this invention, malodour or bad odour is understood in particular the odour of human sweat odour and/or body odour, especially that of the artificial sweat odour composition that humans find unpleasant.

Odour masking, harmonizing or deodorizing is understood as the complete or partial concealing of an odour, in the present case of sweat odour and/or body odour or the artificial sweat odour composition, by another fragrance/flavor or by a fragrance/flavor mixture.

The intensity of a substance or substance mixture describes the intensity of the mixture perceived by odour by trained assessors, irrespective of the quality of the odour as a bad odour or pleasant odour. The stronger a substance or substance mixture smells, the higher the level of intensity.

EXAMPLES

Sensory Identification of Sweat from Test Persons
Sample Preparations: Donors and T-Shirts
Subjects: Thirty-six healthy, male donors between 21-41 years of age were enrolled in the study. Twelve were of African (average age=31.7±2.4), 12 of Caucasian (average age =30.5±1.6), and 12 of East Asian descent (average age=28.7±1.1).

For 7-10 days prior to collection, donors were instructed to bathe/shower with fragrance-free liquid soap/shampoo to reduce the influence of exogenous VOCs from consumer products during analysis. The subjects were also instructed not to use colognes and perfumed sprays during the entirety of the study.

At the end of this period, donors were instructed to wear three tight-fitting T-shirts under their clothing, one per day for three consecutive days, in order to obtain axillary sweat samples. At the end of each day, or after 18 hours of wear, donors were instructed to return the T-shirts to tightly-sealed plastic bags and store them in a freezer at 0° C. Upon completion of the study, the donors returned the T-shirts to the laboratory where they were stored at −80° C. to preserve the integrity of the samples until ready for use. These donor T-shirts were used for the sensory study.

Preparation of the donor T-shirts for the sensory study: The underarm region of the T-shirt samples collected from each individual donor were cut into 4×4 inch squares, for a total of six underarm regions per donor. These sections were then further cut into four equal-1×1 inch size pieces and stored in a −80° C. freezer to preserve the samples. For each ethnicity, super-donors were created by randomly selecting one, 1×1 inch piece of T-shirt from 4 unique body odor donor samples. These samples were placed in a Hefty® bag and stored in a −80° C. freezer until one hour before the sensory examiners arrived.

Selection of Examiners for the Sensory Test
Subjects: A total of 35 people (19 male and 16 females, all subjects were >21 and <50 years old) were recruited for this research, but 11 failed the screening test (each could not identify 0.1% 3-methyl-2-hexenoic acid (3M2H)).

Screening: A 2-Alternative forced choice test (2-AFCT) was used during the screening task. Participants were presented with two, 250 mL clear glass bottles with FEP tubing and Teflon® nosepieces. One bottle contained 2 mL of 0.1% 3M2H in filtered mineral oil while the second bottle contained only filtered mineral oil. Throughout the screening task, two sets of bottles for each concentration were prepared to alternate between trials in order to allow for maximum replenishment of odour in the headspace between sniffs. Participants were instructed to use one nostril, of their choice, to insert the Teflon nosepiece into during the task. The other nostril was held closed. Using E-Prime® a randomized set of 11 trials was then presented at one minute intervals and participants had to correctly identify ≥9 bottles containing the stronger odour, i.e., 3M2H, in order to proceed. Participants also provided confidence ratings after each trial, viz., truly guessing, somewhat confident, or confident. This task was again repeated for an additional 11 trials using 2, 250 mL clear glass bottles containing 2 mL of 0.1% phenethyl alcohol (PEA) in filtered mineral oil versus mineral oil. Again, participants were required to correctly identify 9 or more of the stronger bottles in order to proceed and provided confidence ratings. Finally, participants were given single bottles of 0.1% PEA, 1% PEA, 0.1% 3M2H and 1% 3M2H. These bottles were presented separately, three consecutive times, at one minute intervals and participants were instructed to provide ratings of intensity (on a modified labelled magnitude scale; LMS), pleasantness (on a 23-point bipolar scale), and familiarity (on a 1-100 point scale), which were then averaged. All of these sensory-related tasks were to be repeated in the actual tests of discrimination of ethnicity-derived body odour; hence, this screening session also served as a training session for future test sessions.

Final panels of 12 male and 12 female participants successfully passed the screening test.

Sensory Tests
Again a 2-AFCT was used. Participants were presented, one at a time, with two, 250 mL amber glass bottles with FEP tubing and Teflon nosepieces containing samples from two different ethnic groups. Three sets of bottles for each ethnicity were prepared to alternate between trials in order to allow for maximum replenishment of odour in the headspace between sniffs. Participants were instructed to use one nostril of their choice to insert the Teflon nosepiece into during the task. Using E-Prime, a randomized set of 11 trials were then presented at one minute intervals. Participants were then asked to choose which bottle they preferred by using the same attribute they choose across all 11 trials (strength, pleasantness, intensity, quality, etc.). Participants also provided confidence ratings after each trial—truly guessing, somewhat confident, or confident.

The pairings were presented as follows: (a) Caucasian (CN) vs. Asian (AN), (b) CN vs. African (AA), and (c) AN vs. AA. Finally, participants were given single bottles of each of the three ethnic groups, presented separately, three consecutive times at one minute intervals and instructed to provide ratings of intensity (LMS), pleasantness, and familiarity (scaled from 1 to 100), which were then averaged.

Overall, the results demonstrate that body odor from the three ethnic groups can be readily discriminated. Caucasians and people of African descent produce, on average, significantly greater amounts of odor than do East Asians.

Qualitative Descriptive Analysis (QDA) of Sweat Extracts

A small panel of five individuals (2 females and 3 males) trained in olfactive descriptions, including a professional perfumer, was involved in the QDA. In a first step the extracts were olfactively evaluated regarding general odor quality and common attributes were determined to best describe the odor. Following attributes were chosen: spicy (cumin), cheesy, waxy, rancid, sour, fruity (in the sense of passion fruit or grapefruit). In a second step one or several standards were determined for every attribute. Each standard consisted of a single chemical which ideally was known to be present in genuine human sweat according to analytical results. Smelling sticks with solutions of all chemicals at a given concentration were available to the panelists during sample evaluation. The standards are listed in Table 1 along with the corresponding attributes.

TABLE 1

Attribute in relation to chemical name

| Chemical name | Attributes |
|---|---|
| 3-Methyl-3-hydroxy hexanoic acid | Spicy (cumin, armpit) |
| E-3-Methyl-2-hexenoic acid | Sweat, armpit |
| Z-3-Mercapto-3-methyl hexan-1-ol | Cheesy |
| Isovaleric acid | Sour (cheesy) |
| 2-Methyl butyric acid | Sour (rancid) |
| Hexanoic acid | Sour, (cheesy) |
| Octanoic acid | Rancid (waxy) |
| 4-Ethyl octanoic acid | Cheesy (rancid) |
| Nonanoic acid | Waxy (rancid) |
| Undecanoic acid | Waxy |
| Decanoic acid | Sour fatty citrus (rancid) |
| Butyric acid | Sour (cheesy) |
| 3-Mercapto-1-hexanol | Sulphurous (fruity) |
| 7-octenoic acid | Sour (cheesy) |
| Lactic acid | Slightly sour, dairy |
| Propionic acid | Sour |
| Acetic acid | Sour |

The perceived intensity of the overall smell and the individual attributes were assessed on a scale of 1 (odorless) to 9 (very strong) for which the panel has been trained with different standards (dilution series) prior the evaluation. Finally all samples were rated by the panel in a consensus fashion meaning that each attribute and overall intensity were discussed and a common rating (1-9) was agreed upon to best describe the sample.

Development from the Attributes to the Artificial Sweat Odour Compositions

The odour intensity of the extracts of the individual ethnic group from the sensory test has been also categorized to the attributes in analogy to the chemical substances of table 1. The result is shown in Table 2:

TABLE 2

Attribute in relation to the individual ethnic groups

| | cumin/clove spice | cheesy | waxy | rancid | sour | fruity | overall intensity |
|---|---|---|---|---|---|---|---|
| Caucasian | 4 | 5 | 4 | 5 | 4 | 2 | 5 |
| African | 6 | 4 | 3 | 4 | 6 | 2 | 6 |
| East Asian | 2 | 3 | 4 | 3 | 2 | 1 | 3 |

With the sensory evaluation of the ethnic group three different compositions have been developed. The result is shown in Table 3.

TABLE 3

Artificial sweat odor composition (concentration in % (w/w))

| Name | Caucasian | African American | East Asian |
|---|---|---|---|
| Isovaleric acid | 0.02 | 0.04 | 0.001 |
| 2-Methyl butyric acid | 0.07 | 0.04 | 0 |
| Caproic acid | 0.01 | 0.07 | 0.01 |
| 3-Methyl-2-hexenoic acid | 0.55 | 0.1 | 0.01 |
| Octanoic acid | 0.07 | 0.04 | 0.3 |
| Nonanoic acid | 0.02 | 0.04 | 0.12 |
| 4-Ethyl octanoic acid | 0.06 | 0.02 | 0.2 |
| Decanoic acid | 0.02 | 0.04 | 0.06 |
| 3-Hydroxy-3-methylhexanoic acid | 0.005 | 0.06 | 0 |
| 3-Mercapto-3-methyl-1-hexanol | 0.000005 | 0.00001 | 0 |
| Undecanoic acid | 0.01 | 0.02 | 0 |
| Butyric acid | 0.002 | 0.009 | 0.002 |
| 3-Mercapto-1-hexanol | 0.000005 | 0.00001 | 0 |
| 7-Octenoic acid | 0.05 | 0.05 | 0 |
| Lactic acid | 0 | 0 | 1 |
| Propionic acid | 0 | 0 | 0.002 |
| Acetic acid | 0 | 0 | 0.001 |

What claimed is:

1. An artificial sweat odour composition, consisting of a solvent and
    (i) at least an alkenoic acid compound having 2-10 carbon atoms,
    (ii) at least a saturated aliphatic carboxylic acid compound having 2-15 carbon atoms, and optionally
    (iii) at least one saturated aliphatic hydroxyl carboxylic acid compound having 3-10 carbon atoms, and/or
    (iv) at least one mercapto-alkanol compound having 2-10 carbon atoms.

2. The composition of claim 1, wherein the compounds (i) to (iv) are selected from
    (i) 7-octenoic acid, 3-methyl-2-hexenoic acid;
    (ii) isovaleric acid, 2-methyl butyric acid, hexanoic acid, octanoic acid, nonanoic acid, 4-ethyl octanoic acid, decanoic acid, undecanoic acid, butyric acid, propionic acid, acetic acid;
    (iii) 3-hydroxy-3-methylhexanoic acid, lactic acid; and
    (iv) 3-mercapto-3-methyl-1-hexanol, 3-mercapto-1-hexanol.

3. The composition of claim 1, wherein
    (i) the at least an alkenoic acid compound is 3-methyl-2-hexenoic acid, and
    (ii) the at least a saturated aliphatic carboxylic acid compound is a mixture of isovaleric acid, hexanoic acid, octanoic acid, nonanoic acid, 4-ethyl octanoic acid, decanoic acid and butyric acid.

4. The composition of claim 1, wherein
    (i) the at least alkenoic acid compound is 3-methyl-2-hexenoic acid,
    (ii) the at least saturated aliphatic carboxylic acid compound is a mixture of isovaleric acid, hexanoic acid, octanoic acid, nonanoic acid, 4-ethyl octanoic acid, decanoic acid, butyric acid, propionic acid and acetic acid, and
    (iii) the at least saturated aliphatic hydroxyl carboxylic acid compound is lactic acid.

5. The composition of claim 1, wherein
    (i) the at least alkenoic acid compound further comprises oct-7-enoic acid,
    (ii) the at least saturated aliphatic carboxylic acid compound further comprises 2-methylbutyric acid, undecanoic acid, butyric acid, (iii) the at least saturated aliphatic hydroxyl carboxylic acid compound is 3-hydroxy-3-methylhexanoic acid, and (iv) the at least one mercapto-alkanol compound is a mixture of 3-mercapto-1-hexanol and 3-mercapto-3-methyl-1-hexanol.

6. The composition of claim 1, wherein the composition comprises
(a) 3-methyl-2-hexenoic acid as alkenoic acid compound having 2-10 carbon atoms; and
(b) a mixture of octanoic acid and nonanoic acid as saturated aliphatic carboxylic acid compounds having 2-15 carbon atoms.

7. The composition of claim 1, wherein the composition comprises
(a) 3-methyl-2-hexenoic acid as alkenoic acid compound having 2-10 carbon atoms,
(b) 3-hydroxy-3-methylhexanoic acid as saturated aliphatic hydroxyl carboxylic acid compound having 3-10 carbon atoms, and
(c) 3-mercapto-3-methyl-l-hexanol as mercapto-alkanol compound having 2-10 carbon atoms.

8. The composition of Claim 1, wherein the solvent is selected from the group consisting of trialkyl citrates, dialkylphthalates, alcohols, fatty oils, propylene glycol, glycerine diacetate, glycerine triacetate, ethyl lactate, glycerine, mineral oil, and mixtures thereof.

9. The composition of claim 1, wherein the total amount of all compounds (i) to (iv) in the composition is in the range from 0.1 to 5% by weight, based on the total weight of the composition, and thus the solvent sums up the total weight of the composition to 100% by weight.

10. A. scent /smell pen comprising the artificial sweat odour composition of claim 1.

11. A method for evaluating an effect of masking, harmonizing or deodorizing to a body odour by a sample comprising one or more flavours or fragrances, comprising the following steps:
(a) providing an artificial sweat odour composition according to claim 1,
(b) bringing the artificial sweat odour composition of step a) in contact with the flavour or fragrance sample which is to be evaluated, and
(c) determining the intensity and/ or malodour impression of the artificial sweat odour composition in comparison to the flavour or fragrance sample which is to be evaluated.

* * * * *